(12) United States Patent  
Alkhatib et al.

(10) Patent No.: US 8,926,679 B2
(45) Date of Patent: Jan. 6, 2015

(54) BIFURCATED STENT SYSTEM BALLOON FOLDS

(75) Inventors: Yousef Alkhatib, Maple Grove, MN (US); Adam Jennings, Buffalo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 925 days.

(21) Appl. No.: 11/368,083

(22) Filed: Mar. 3, 2006

(65) Prior Publication Data

US 2007/0208406 A1     Sep. 6, 2007

(51) Int. Cl.
| | |
|---|---|
| *A61F 2/06* | (2013.01) |
| *A61F 2/954* | (2013.01) |
| *A61F 2/958* | (2013.01) |
| *A61F 2/856* | (2013.01) |

(52) U.S. Cl.
CPC ............... *A61F 2/954* (2013.01); *A61F 2/958* (2013.01); *A61F 2/856* (2013.01)
USPC .......... 623/1.11; 623/1.35; 606/108; 606/194

(58) Field of Classification Search
USPC ........ 623/1.11, 1.35; 604/96.01, 103–103.14; 606/191–200
See application file for complete search history.

(56) References Cited

U.S. PATENT DOCUMENTS

| | | | |
|---|---|---|---|
| 5,242,399 A * | 9/1993 | Lau et al. ..................... 604/104 |
| 5,342,307 A | 8/1994 | Euteneuer et al. | |
| 5,350,361 A | 9/1994 | Tsukashima et al. | |
| 5,350,395 A * | 9/1994 | Yock ............................. 606/194 |
| 5,456,666 A | 10/1995 | Campbell et al. | |
| 5,681,345 A | 10/1997 | Euteneuer | |
| 5,690,642 A * | 11/1997 | Osborne et al. .............. 623/1.11 |
| 5,788,707 A | 8/1998 | Del Toro et al. | |
| 5,797,878 A * | 8/1998 | Bleam ........................... 604/196 |
| 5,968,069 A | 10/1999 | Dusbabek et al. | |
| 6,007,517 A * | 12/1999 | Anderson ................. 604/103.04 |
| 6,013,055 A | 1/2000 | Bampos et al. | |
| 6,013,092 A * | 1/2000 | Dehdashtian et al. ........ 606/194 |
| 6,056,775 A | 5/2000 | Borghi et al. | |
| 6,066,155 A | 5/2000 | Amann et al. | |
| 6,071,285 A * | 6/2000 | Lashinski et al. ............ 623/1.11 |
| 6,190,353 B1 | 2/2001 | Makower et al. | |
| 6,203,568 B1 | 3/2001 | Lombardi et al. | |
| 6,210,429 B1 | 4/2001 | Vardi et al. | |
| 6,221,097 B1 | 4/2001 | Wang et al. | |
| 6,280,412 B1 | 8/2001 | Pederson, Jr. et al. | |

(Continued)

FOREIGN PATENT DOCUMENTS

| | | | | |
|---|---|---|---|---|
| EP | 1 308 139 A2 | 5/2003 | | |
| EP | 1308139 A2 * | 5/2003 | ............... | A61F 2/06 |
| WO | WO 03/105922 A2 | 12/2003 | | |
| WO | WO 03/105992 | * 12/2003 | | |

*Primary Examiner* — Mark Mashack

(74) *Attorney, Agent, or Firm* — Seager, Tufte & Wickhem LLC

(57) ABSTRACT

The present invention is directed to balloon folding configurations and methods for catheter devices having dual lumens in radial proximity to the balloon, such as, but not limited to, self-aligning stent delivery systems for treatment of bifurcated lesions. The configuration designs alters the conventional catheter profile by packing balloon materials in otherwise vacant areas located on both sides of the side branch shaft and/or the parent shaft, such that the device takes on more of a round profile instead of the classical elongated egg-shaped profile.

11 Claims, 12 Drawing Sheets

(56) References Cited

U.S. PATENT DOCUMENTS

| | | |
|---|---|---|
| 6,331,186 B1 | 12/2001 | Wang et al. |
| 6,342,066 B1 | 1/2002 | Toro et al. |
| 6,346,089 B1 | 2/2002 | Dibie |
| 6,350,277 B1 | 2/2002 | Kocur |
| 6,443,880 B2 | 9/2002 | Blais et al. |
| 6,478,814 B2 | 11/2002 | Wang et al. |
| 6,540,779 B2 | 4/2003 | Richter et al. |
| 6,596,020 B2 | 7/2003 | Vardi et al. |
| 6,599,315 B2 | 7/2003 | Wilson |
| 6,663,660 B2 | 12/2003 | Dusbabek et al. |
| 6,955,687 B2 | 10/2005 | Richter et al. |
| 6,955,688 B2 | 10/2005 | Wilson et al. |
| 6,962,602 B2 | 11/2005 | Vardi et al. |
| 2003/0163157 A1* | 8/2003 | McMorrow et al. .......... 606/194 |
| 2004/0143286 A1* | 7/2004 | Johnson et al. ............... 606/194 |
| 2004/0172119 A1 | 9/2004 | Eidenschink |
| 2004/0172121 A1 | 9/2004 | Eidenschink |
| 2005/0149161 A1 | 7/2005 | Eidenschink |
| 2005/0154442 A1 | 7/2005 | Eidenschink |
| 2005/0183259 A1 | 8/2005 | Eidenschink |
| 2005/0273149 A1 | 12/2005 | Tran |
| 2006/0030924 A1* | 2/2006 | Van Der Leest et al. .... 623/1.11 |
| 2006/0100694 A1* | 5/2006 | Globerman ................. 623/1.35 |

* cited by examiner

BIFURCATED STENT SYSTEM BALLOON FOLDS

FIELD OF THE INVENTION

This invention relates to balloon folding configurations for balloon catheter systems having distal dual lumens.

BACKGROUND OF THE INVENTION

Percutaneous transluminal coronary angioplasty (PTCA) is a procedure that is well established for the treatment of blockages, lesions, stenosis, thrombus, etc. present in body lumens such as the coronary arteries and/or other vessels.

A widely used form of percutaneous coronary angioplasty makes use of a dilatation balloon catheter, which is introduced into and advanced, through a lumen or body vessel until the distal end thereof is at a desired location in the vasculature. Once in position across an afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilatation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Stents, grafts, stent-grafts, vena cava filters, expandable frameworks, and similar implantable medical devices, collectively referred to herein as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Prior to delivery, a stent or stents may be retained on a portion of the delivery catheter by crimping the stent onto the catheter, retaining the stent in a reduced state about the catheter with a removable sheath, sleeve, sock or other member or members, or by any of a variety of retaining mechanisms or methods. Some examples of stent retaining mechanisms are described in U.S. Pat. No. 5,681,345; U.S. Pat. No. 5,788,707; U.S. Pat. No. 5,968,069; U.S. Pat. No. 6,066,155; U.S. Pat. No. 6,096,045; U.S. Pat. No. 6,221,097; U.S. Pat. No. 6,331,186; U.S. Pat. No. 6,342,066; U.S. Pat. No. 6,350,277; U.S. Pat. No. 6,443,880; and U.S. Pat. No. 6,478,814.

Bodily vessels that branch off into further vessels are termed bifurcated vessels. Some bifurcated vessels have stenotic lesions and disease requiring treatment of the parent vessel, while preserving access to the side branch vessel. A dual lumen catheter system used to stent a bifurcation site allows the physician to maintain guide wires in both the parent and side branch vessels. These guide wires can then allow post dilation balloons to be guided into the bifurcation through a deployed stent. In a dual lumen device, the stent cell that the side branch lumen penetrates aligns itself into the side branch vessel. Proper alignment assures that the carina gets good stent coverage and that the stent does not obstruct the side branch vessel.

A stent delivery system employing a stent assembly with branches intended for deployment in adjacent branches of a vessel bifurcation allows placement of a portion of the assembly in both a primary passage, such as an artery, and a secondary passage, such as a side branch artery. Additionally, these stents generally have an opening that allows for unimpeded blood flow into the side branch artery. However, due to use of two separate lumens, the resulting profile is increased and the cross-section takes on an oval shape, reducing stent contact and ease of stent rotation.

Thus, a need exists to provide a catheter that is capable of allowing a medical device, such as a stent, to be easily maneuvered and aligned at a vessel bifurcation or other location. Various devices and methods described herein address these issues by providing a catheter system with inventive balloon folding designs.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to stent delivery systems having unique balloon configurations and methods for catheter devices having dual lumens in radial proximity to the balloon, such as, but not limited to, self-aligning stent delivery systems for treatment of bifurcated lesions. The configuration designs alter the conventional catheter profile by packing balloon materials in otherwise vacant areas located on both sides of the side branch shaft and/or the parent shaft, such that the device takes on more of a round profile instead of the classical elongated egg-shaped profile. With the round profile, the stent achieves more uniform deployment characteristics and decreases the resistance of the device when rotating in the vessel. Decreasing the resistance to rotate the stent into alignment allows the device to align with less input force from the physician.

In at least some embodiments, the round profile also enhances stent securement. With a round profile, one may better utilize crimping processes without worry about major and minor axis crimp force applied. Crimp head elements of conventional crimpers can close on a round profile uniformly, thus maximizing stent strut contact with the balloon material. Furthermore, in embodiments where the balloon folds surround the side branch shaft, the crimped stent makes contact with balloon material all the way around creating a pillowing effect for increased securement.

The folding configurations of the present invention also accommodate radial alignment of the distal end of the catheter due to the presence of balloon material between the crimped stent and the side branch shaft. A radially aligned side branch shaft is parallel to the parent shaft and properly positioned relative to the stent so as to extend through the stent into a side branch vessel. Additional stiffness transition can also be provided at the side branch shaft exit location. Balloon folds create walls on either side of the side branch shaft limiting the side-to-side motion of the side branch. Limiting side-to-side motion allows for an increase in torque transmission to align the stent with the side branch vessel.

In at least one embodiment, the stent-receiving region of a stent delivery system of the present invention comprises a parent shaft and a side branch shaft aligned in parallel fashion and a stent mounted there about. A balloon is mounted about the parent shaft and is positioned between the two shafts. When the balloon is in its delivery configuration, it comprises at least two inward wing folds extending from the central body of the balloon. The two wing folds are inwardly wrapped on both sides of the side branch shaft.

In at least one embodiment, the stent-receiving region of a stent delivery system of the present invention comprises a parent shaft and a side branch shaft aligned in parallel fashion and a stent mounted there about. A balloon is mounted about the parent shaft and is positioned between the two shafts. When the balloon is in its delivery configuration, it comprises two outward wing folds extending from the central body of the balloon. The two wing folds are outwardly wrapped on both sides of the side branch shaft.

In at least one embodiment, the stent-receiving region of a stent delivery system of the present invention comprises a parent shaft and a side branch shaft aligned in parallel fashion and a stent mounted there about. A balloon is mounted about the parent shaft and is positioned between the two shafts. When the balloon is in its delivery configuration, it comprises two inward wing folds extending from the central body of the balloon. The two wing folds are inwardly wrapped over the side branch shaft in overlapping fashion.

In at least one embodiment, the stent-receiving region of a stent delivery system of the present invention comprises a parent shaft and a side branch shaft aligned in parallel fashion and a stent mounted there about. A balloon is mounted about the parent shaft and at least a portion is positioned between the two shafts. When the balloon is in its delivery configuration, it comprises three inward wing folds extending from the central body of the balloon. Two wing folds are inwardly wrapped on both sides of the side branch shaft. The third wing is formed at the six-o'clock orientation (from a cross-sectional view prospective, wherein the side branch shaft is in the twelve-o'clock position relative the parent shaft). It should be understood that more than three wing folds may be employed at varying positions around the parent shaft.

In at least one embodiment, the stent-receiving region of a stent delivery system of the present invention comprises a parent shaft and a side branch shaft aligned in parallel fashion and a stent mounted there about. A balloon is mounted about the parent shaft and at least a portion is positioned between the two shafts. When the balloon is in its delivery configuration, it comprises three outward wing folds extending from the central body of the balloon. Two wing folds are outwardly wrapped on both sides of the side branch shaft. The third wing is formed at the six-o'clock orientation (from a cross-sectional view prospective, wherein the side branch shaft is in the twelve-o'clock position relative the parent shaft). It should be understood that more than three wing folds may be employed at varying positions around the parent shaft.

These and other embodiments that characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
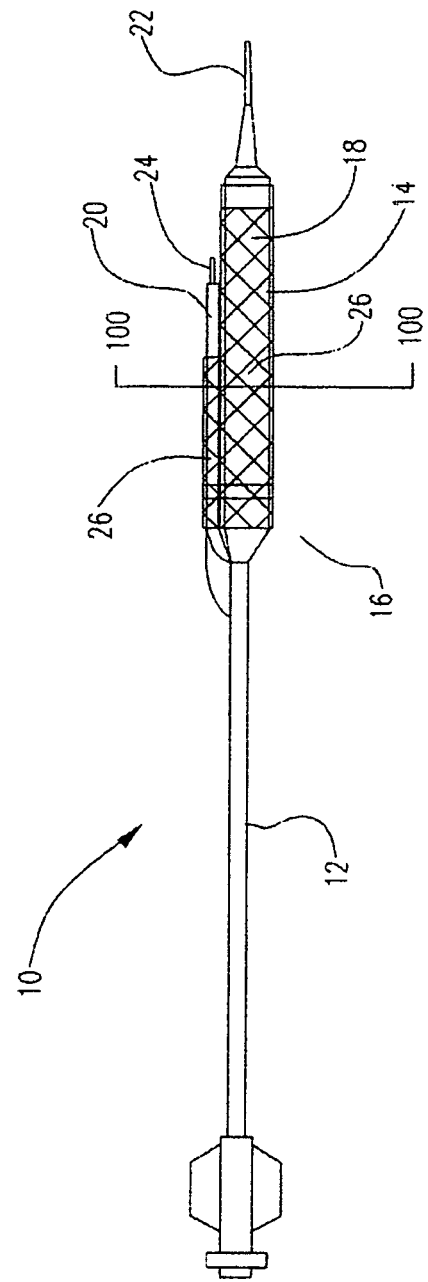
FIG. 1 is a side view of a dual lumen stent delivery system.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to the drawings, which are for the purposes of illustrating embodiments of the invention only and not for purposes of limiting same, FIG. 1 illustrates a dual lumen stent delivery system 10. This illustrative representation is being used to generally refer to bifurcated systems having dual lumens for dual guide wires, a primary guidewire 22 and a secondary guidewire 24, for accessing bifurcated vessels. Examples of bifurcated systems include, but are not limited to, those shown and described in U.S. patent application Ser. No. 10/375,689, filed Feb. 27, 2003 and U.S. patent application Ser. No. 10/657,472, filed Sep. 8, 2003, both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; and U.S. patent application Ser. No. 10/757,646, filed Jan. 13, 2004 and entitled Bifurcated Stent Delivery System, the entire content of each being incorporated herein by reference.

The inventive system 10 includes a catheter 12 having a balloon 14 mounted on the distal end 16. At the distal end 16 end of the catheter, there are two radially adjacent shafts 18, 20. As shown in FIG. 1, the balloon 14 is mounted on shaft 18, which is the parent shaft. Shaft 18 defines a lumen, which houses a primary guide wire 22. Branching off of the parent shaft 18 or at some other position on the catheter 12 is a side branch shaft 20. Side branch shaft 20 also defines a lumen, which houses a second or secondary guide wire 24. The construction and use of such dual lumen catheters are well known to those skilled in the art of catheter design and use.

Figure 2:
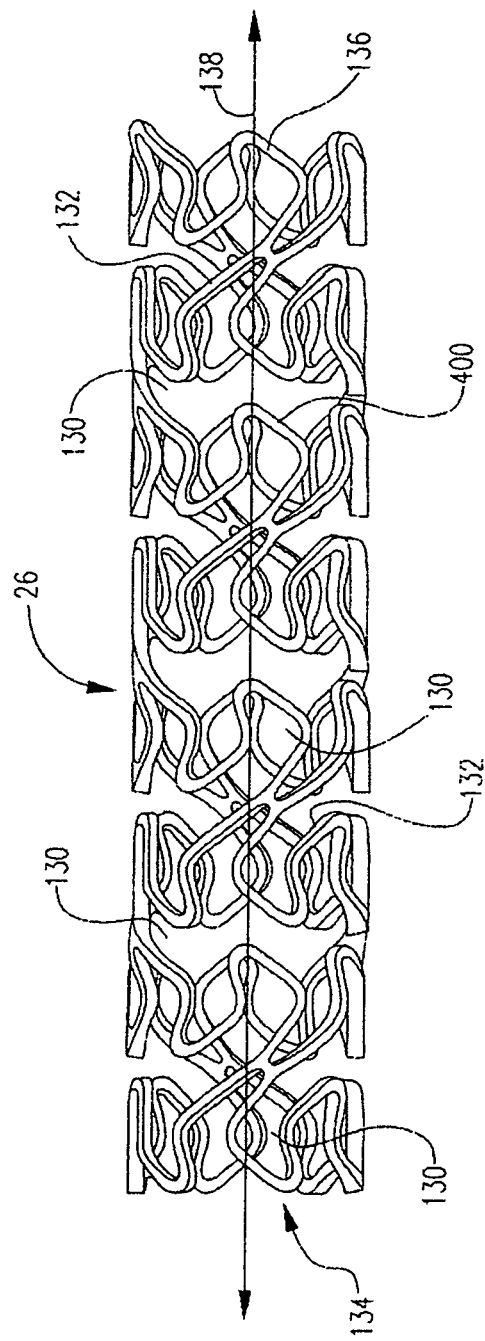
FIG. 2 is a side perspective view of a stent, such as that shown in FIG. 1.

As shown in FIG. 1, a stent 26 is mounted onto the balloon 14 and parent shaft 18 and onto the side branch shaft 20. Stent 26 may be a stent, such as is shown in FIG. 2, which is at least partially constructed of a plurality of interconnected struts, connectors or members 132. The stent 132 defines a proximal opening 134, a distal opening 136 and a flow path 138 there between. The cell openings 130 are in fluid communication with the flow path 138.

When the secondary guidewire 24 and/or the side branch shaft 20 is threaded through one of the cell openings 130 when the stent is positioned onto the assembly 10, such as is shown in FIG. 1, the members 132 that define the selected cell opening 130a, as well as the shape of the opening 130a through which the secondary guidewire 24 exits the stent, may be distorted or modified in order to accommodate the passage of secondary guidewire 24 and/or the side branch shaft 20 there through.

Figure 3:
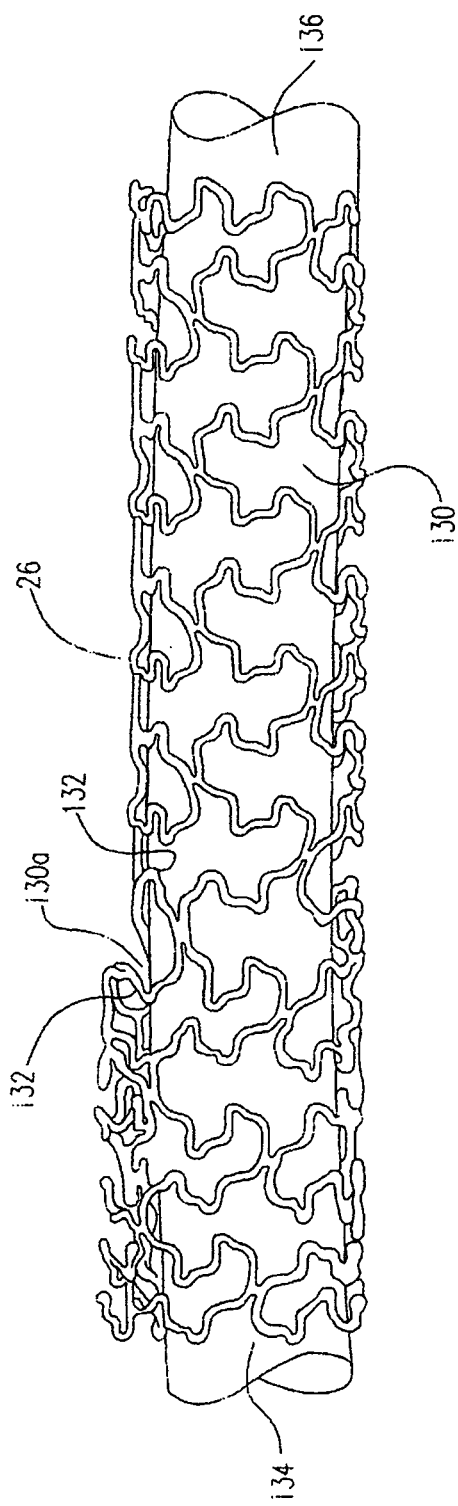
FIG. 3 is a side perspective view of the stent shown in FIG. 2, wherein a side branch opening is shown formed.
Figure 4:
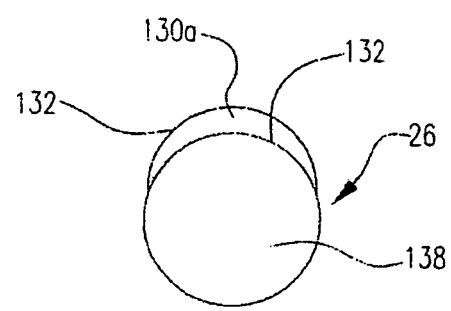
FIG. 4 is a cross-sectional view of the stent of FIG. 3.

The modified cell opening 130a, hereinafter referred to as secondary opening 130a, is positioned on the stent 26 between the proximal opening 134 and the distal opening 136. The manner in which the secondary opening 130a, the members 132 adjacent thereto, and to an extent the stent 26 itself, are modified or distorted by the position of the secondary guidewire 24 and/or side branch shaft 20 is depicted in FIGS. 3 and 4.

It should be noted that when the stent 26 is placed on the assembly in the manner described above, the distortion of the secondary opening 130a and the adjacent members 132 is of a minimal extent, and is provide only to allow sliding passage of the secondary guidewire 24, and if desired a distal portion of the side branch shaft 20, through the secondary opening 130a. As such, the actual size of the secondary opening 130a may be substantially similar, or only marginally different than that of the surrounding cell openings 130.

It should also be further noted that while stent 26 may be a standard "single vessel" stent that is provided with a secondary opening 130a in the manner described above, the stent 26 may also be a bifurcated stent having a trunk or stem portion, with one or more leg portions and/or branch openings adjacent thereto, through one of which the secondary guidewire may be passed. Such bifurcated stents and stent assemblies are well known in the art.

In some cases, the stent 26 may be configured to deliver one or more therapeutic agents to a delivery site such as within the vessel or one or more areas adjacent thereto. To better accommodate placement of a therapeutic agent on the stent 26, in some instances one or more stent members 132, such as is shown in FIG. 2, maybe configured to include one or more holes, notches, or other surface features to which one or more therapeutic agents 400 may be placed for delivery to the aneurysm site. A therapeutic agent may be placed on the stent in the form of a coating. Often the coating includes at least one therapeutic agent and at least one polymer.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic includes cellular material, the cellular material may include but is not limited to: cells of human origin and/or non-human origin as well as their respective components and/or derivatives thereof. Where the therapeutic agent includes a polymer agent, the agent may be a polystyrene-polyisobutylene-polystyrene triblock copolymer (SIBS), polyethylene oxide, silicone rubber and/or any other suitable substrate.

Figure 5:
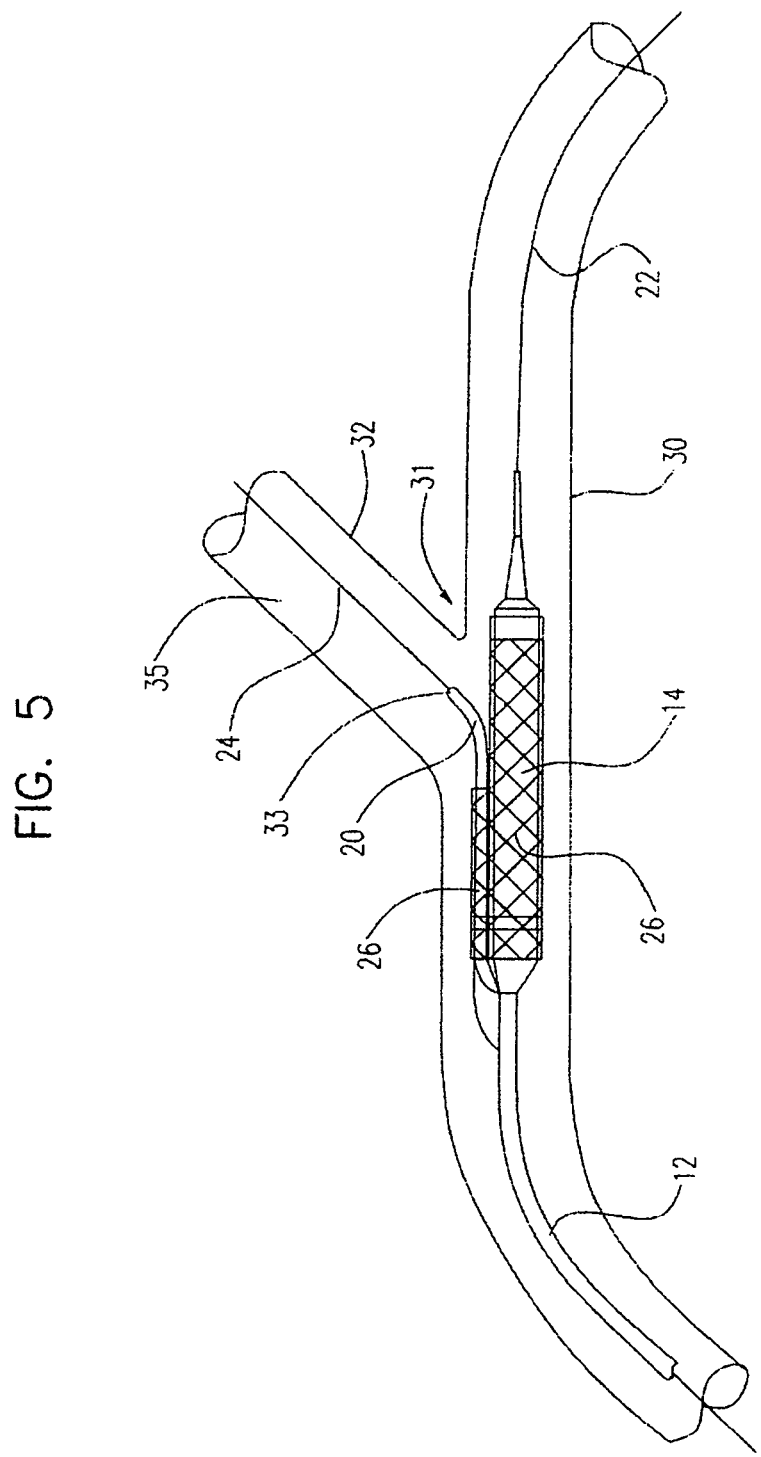
FIG. 5 is a side view of a stent delivery catheter within a bifurcated vessel.

As shown in FIG. 5, in use, the catheter 12 is inserted into a vessel 30 and advanced along the primary guide wire 22 to a portion 31 of the vessel 30, which is bifurcated. The end 33 of the side branch shaft 24 is positioned at the opening of the branching vessel 32 so that the secondary guide wire 24 may be advanced into the branching vessel 32. In some bifurcation systems, including, but not limited to, the system described in U.S. patent application Ser. No. 10/863,724, titled BIFURCATED STENT DELIVERY SYSTEM, which is incorporated herein by reference in its entirety, as the system is advanced along both guidewires 22 and 24, as a result of the divergent paths defined by the guidewires 22 and 24, the stent 26 is moved into a desired position so that the secondary opening 130a of the stent is aligned with the secondary passage 35.

FIGS. 6-12 are illustrations of various configurations of the invention. The figures show cross-sectional views of the system 10 shown in FIG. 1 along lines 100-100. The illustrations show the folding and positioning of the balloon 14 relative to the parent shaft 18, the side branch shaft 20 and the stent 26, when the balloon 14 and stent 26 are in their delivery configuration during placement of the catheter. The folds extend along the length of the balloon 14. The illustrations are illustrative and aren't meant to be to scale. Techniques for folding balloons are well known and therefore are not discussed herein.

Figure 6:
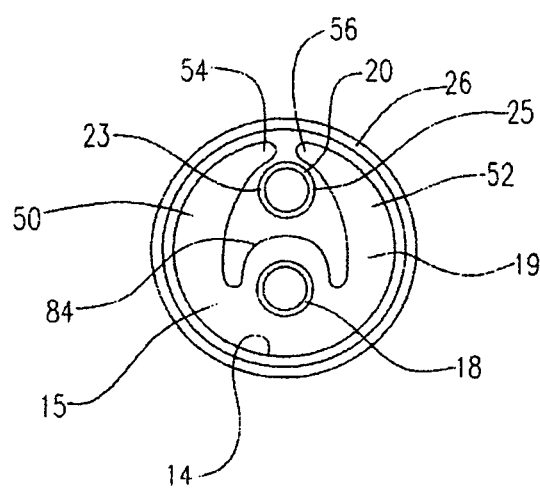
FIG. 6 is a cross-sectional view of an embodiment of the catheter shown in FIG. 1 along lines 100-100.

In the embodiment shown in FIG. 6, the balloon 14 and shafts 18 and 20 are positioned within contracted stent 26. As mentioned above, the balloon 14 is positioned about the parent shaft 18 and the side branch shaft 20 is positioned outside of the balloon 14, such that a portion of the balloon 14 is between the side branch shaft 20 and the parent shaft 18. The side branch shaft 20 is outside of the inner space 15 of the balloon 14. The balloon is folded, such that two wing folds 50, 52, are created. Although the illustrations show space 19 within the wing folds, it should be understood that, when the balloon 14 is deflated, the wings may flatten and extend from a central body 84, which is formed from the balloon material deflated around and close to the parent shaft 18. The wing folds 50, 52, axially extend along the length of the balloon 14. The wing folds 50, 52, are folded such that they are wrapped inward and extend from the parent shaft 18 toward and on either side 23, 25, of the side branch shaft 20. The ends 54, 56, of the wing folds 50, 52, may extend up to the sides of the side branch shaft 20 or they may extend up and over the side branch shaft 20, such that the ends 54, 56, are in immediate proximity, up to the point of touching each other.

Figure 7:
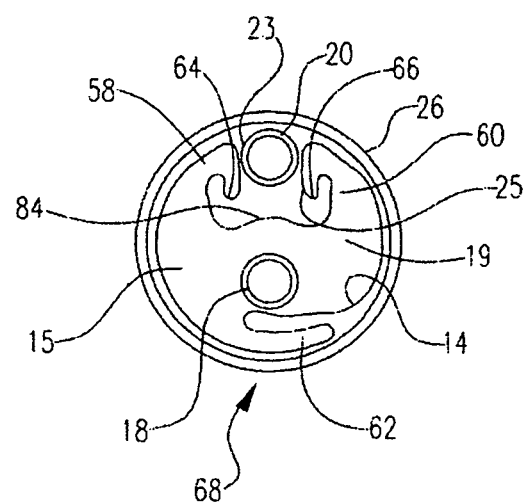
FIG. 7 is a cross-sectional view of an embodiment of the catheter shown in FIG. 1 along lines 100-100.

In the embodiment shown in FIG. 7, the balloon 14 and shafts 18 and 20 are positioned within contracted stent 26. As mentioned above, the balloon 14 is positioned about the parent shaft 18 and the side branch shaft 20 is positioned outside of the balloon 14, such that a portion of the balloon 14 is between the side branch shaft 20 and the parent shaft 18. The side branch shaft 20 is outside of the inner space 15 of the balloon 14. The balloon is folded, such that three wing folds 58, 60, 62, are created. Although the illustrations show space 19 within the wing folds, it should be understood that, when the balloon 14 is deflated, the wings may flatten and extend from a central body 84, which is formed from the balloon material deflated around and close to the parent shaft 18. The wing folds 58, 60, 62, axially extend along the length of the balloon 14. The wing folds 58, 60, are folded such that they are wrapped inward and extend from the parent shaft 18 toward and on either side 23, 25, of the side branch shaft 20. The ends 64, 66, of the wing folds 50, 52, may extend up to the sides of the side branch shaft 20 or they may extend up and over the side branch shaft 20, such that the ends 64, 66, are in immediate proximity, up to the point of touching each other or they may curl inward, as shown in FIG. 7. The third wing fold 62 is positioned at a 6-oclock orientation 68 from a cross-sectional view perspective and is wrapped in either a clockwise or a counter clockwise direction. Wing folds 50, 52, may be as long as or longer than wing fold 62.

Figure 8:
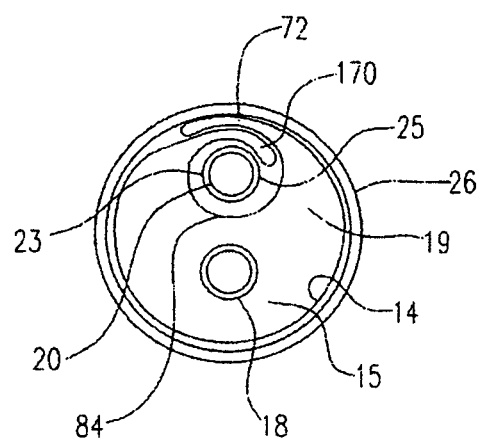
FIG. 8 is a cross-sectional view of an embodiment of the catheter shown in FIG. 1 along lines 100-100.

In the embodiment shown in FIG. 8, the balloon 14 and shafts 18 and 20 are positioned within contracted stent 26. As mentioned above, the balloon 14 is positioned about the parent shaft 18 and the side branch shaft 20 is positioned outside of the balloon 14, such that a portion of the balloon 14 is between the side branch shaft 20 and the parent shaft 18. The side branch shaft 20 is outside of the inner space 15 of the balloon 14. The balloon is folded, such that two wing folds 70, 72, are created. Although the illustrations show space 19 within the wing folds, it should be understood that, when the balloon 14 is deflated, the wings may flatten and extend from a central body 84, which is formed from the balloon material deflated around and close to the parent shaft 18. The wing folds 70, 72, axially extend along the length of the balloon 14. The wing folds 70, 72, are folded such that they are wrapped inward and extend from the parent shaft 18 toward and on either side 23, 25, of the side branch shaft 20. The wing folds 70, 72, extend up and over the side branch shaft 20, to an extent such that the wing folds 70, 72, overlap each other.

Figure 9:
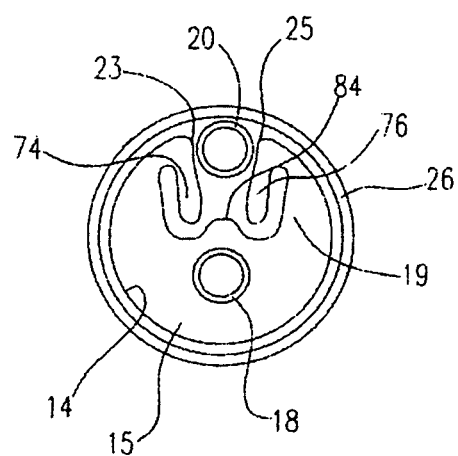
FIG. 9 is a cross-sectional view of an embodiment of the catheter shown in FIG. 1 along lines 100-100.

In the embodiment shown in FIG. 9, the balloon 14 and shafts 18 and 20 are positioned within contracted stent 26. As mentioned above, the balloon 14 is positioned about the parent shaft 18 and the side branch shaft 20 is positioned outside of the balloon 14, such that a portion of the balloon 14 is between the side branch shaft 20 and the parent shaft 18. The side branch shaft 20 is outside of the inner space 15 of the balloon 14. The balloon is folded, such that two wing folds 74, 76, are created. Although the illustrations show space 19 within the wing folds, it should be understood that, when the balloon 14 is deflated, the wings may flatten and extend from a central body 84, which is formed from the balloon material deflated around and close to the parent shaft 18. The wing folds 74, 76, axially extend along the length of the balloon 14. The wing folds 74, 76, are folded such that they are wrapped inward and extend from the parent shaft 18 toward and on either side 23, 25, of the side branch shaft 20. The wing folds 74, 76, curl inward to the parent shaft 18 on either side 23, 25, of the side branch shaft 20.

Figure 10:
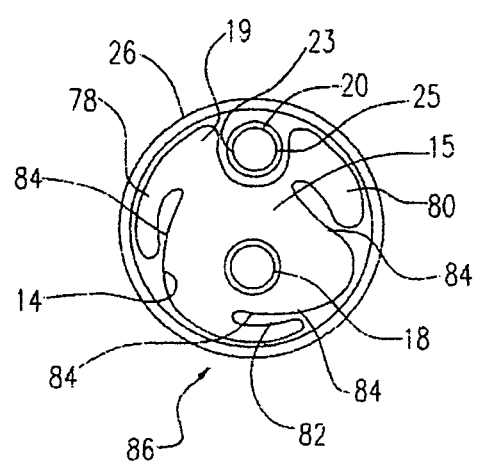
FIG. 10 is a cross-sectional view of an embodiment of the catheter shown in FIG. 1 along lines 100-100.

In the embodiment shown in FIG. 10, the balloon 14 and shafts 18 and 20 are positioned within contracted stent 26. As mentioned above, the balloon 14 is positioned about the parent shaft 18 and the side branch shaft 20 is positioned outside of the balloon 14, such that a portion of the balloon 14 is between the side branch shaft 20 and the parent shaft 18. The side branch shaft 20 is outside of the inner space 15 of the balloon 14. The balloon is folded, such that three wing folds 78, 80, 82, are created. Although the illustrations show space 19 within the wing folds, it should be understood that, when the balloon 14 is deflated, the wings may flatten and extend from a central body 21, which is formed from the balloon material deflated around and close to the parent shaft 18. The wing folds 78, 80, 82, axially extend along the length of the balloon 14. The wing folds 78, 80, are folded such that they extend from the parent shaft 18 toward and on either side 23, 25, of the side branch shaft 20 and are wrapped outward and down, overlapping the central body 84 of the balloon 14. The third wing fold 82 is positioned at a 6-oclock orientation 68 from a cross-sectional view perspective and is wrapped in either a clockwise or a counter clockwise direction. Wing folds 50, 52, may be as long as or longer than wing fold 62 or wing fold 62 may be longer than wing folds 50, 52.

Figure 11:
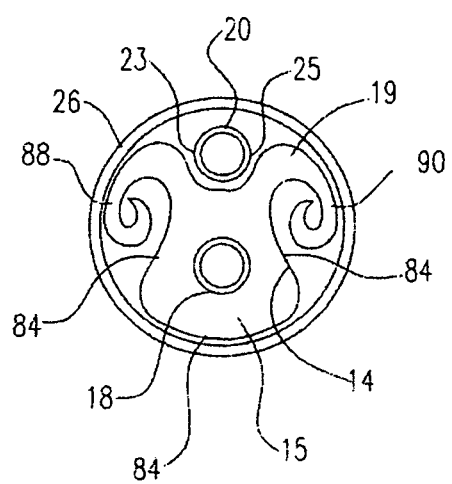
FIG. 11 is a cross-sectional view of an embodiment of the catheter shown in FIG. 1 along lines 100-100.

In the embodiment shown in FIG. 11, the balloon 14 and shafts 18 and 20 are positioned within contracted stent 26. As mentioned above, the balloon 14 is positioned about the parent shaft 18 and the side branch shaft 20 is positioned outside of the balloon 14, such that a portion of the balloon 14 is between the side branch shaft 20 and the parent shaft 18. The side branch shaft 20 is outside of the inner space 15 of the balloon 14. The balloon is folded, such that two wing folds 88, 90, are created. Although the illustrations show space 19 within the wing folds, it should be understood that, when the balloon 14 is deflated, the wings may flatten and extend from a central body 21, which is formed from the balloon material deflated around and close to the parent shaft 18. The wing folds 88, 90, axially extend along the length of the balloon 14. The wing folds 88, 90, are folded, such that they extend from the parent shaft 18 toward and on either side 23, 25, of the side branch shaft 20 and are wrapped outward and down, overlapping the central body 84 of the balloon 14. The wing folds 88, 90, curl inward on itself toward the parent shaft 18 on either side of the central body 84.

Figure 12:
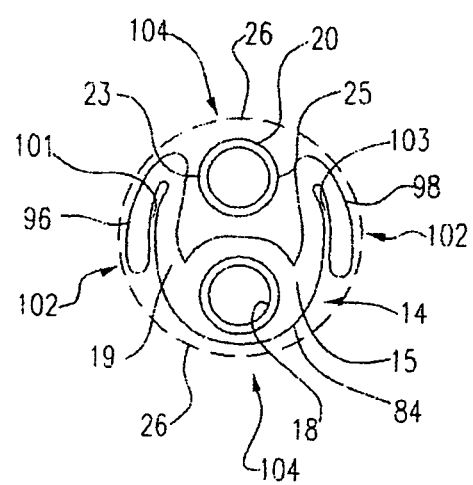
FIG. 12 is a cross-sectional view of an embodiment of the catheter shown in FIG. 1 along lines 100-100.

In the embodiment shown in FIG. 12, the balloon 14 and shafts 18 and 20 are positioned within contracted stent 26. As mentioned above, the balloon 14 is positioned about the parent shaft 18 and the side branch shaft 20 is positioned outside of the balloon 14, such that a portion of the balloon 14 is between the side branch shaft 20 and the parent shaft 18. The side branch shaft 20 is outside of the inner space 15 of the balloon 14. The balloon is folded, such that two wing folds 96, 98, are created. Although the illustrations show space 19 within the wing folds, it should be understood that, when the balloon 14 is deflated, the wings may flatten and extend from a central body 21, which is formed from the balloon material deflated around and close to the parent shaft 18. The wing folds 96, 98, axially extend along the length of the balloon 14. The wing folds 92, 94, are folded, such that they extend up from the sides of the parent shaft 18 toward and on either side 23, 25, of the side branch shaft 20 and are wrapped outward and down, overlapping themselves. As with the other embodiments, the majority of the balloon 14 material is positioned on the sides 101, 103, of the parent shaft 18/side branch shaft 20 combination, increasing the minor axis 102 and decreasing the major axis 104. The device thereby becomes more circular and more symmetrical, reducing the maximum profile. Increasing the balloon fold material on the sides increases the surface area that the stent 26 has to grip to, increasing stent securement.

In FIGS. 6, 9, 11, and 12, the balloon folds are symmetrical. As the balloon unwraps during deployment, the torque caused by the friction between the balloon folds and stent rotation are neutral due to cancellation of opposite forces. Due to the symmetry in the proposed fold designs, the balloon unfolds in a manor that preserves the radial location of the bifurcated stent just prior to deployment. The prevention of device rotation allows the aligning of the stent to the opposing side branch vessel.

The symmetrical balloon folds eliminate any radial motion of the stent from pre-deployment to the stent being opposed to the vessel wall. The function of minimizing balloon material on the major axis and maximizing it on the minor axis is to reduce profile and gain more uniform stent securement. The symmetrical wing fold designs generate forces in opposite directions thus holding the radial position of the delivery system and stent. Having balloon material over the side branch lumen allows for higher stent securement and complete 360 degree cone puffing, as shown in FIGS. 6 and 8.

The folds of the embodiments provide a more circular profile once the stent is crimped on and provide radial support for the side branch lumen. A more circular profile is more compatible with existing stent crimping and processing equipment. As shown in some figures, such as FIGS. 6 and 8, the design allows the stent to have complete contact with the balloon material, thus increasing stent securement performance. Also, having balloon folds over the side branch lumen enhances the edge protection performance.

The present invention also contemplates a stent securement component coaxially mounting on the parent shaft 18 within the balloon 14. Such securement components are described in U.S. Pat. No. 6,663,660, which is herein incorporated in its entirety.

The catheter shafts may be constructed of any of a variety of suitable materials such as: PEBAX, nylon, urethane, and/or other materials in a single layer, multi-layer and/or braided configuration.

Balloon 14 may be a typical angioplasty, stent delivery balloon or other inflatable member, which may be used or incorporated into a catheter assembly. The balloon 14 may be constructed of any suitable balloon material known to those of skill in the art. Commonly employed materials include the thermoplastic elastomeric and non-elastomeric polymers and the thermosets including the moisture curable polymers. Examples of suitable materials include but are not limited to, polyolefins, polyesters, polyurethanes, polyamides, polyimides, polycarbonates, polyphenylene sulfides, polyphenylene oxides, polyethers, silicones, polycarbonates, styrenic polymers, polytetraflouroethylene, copolymers thereof, and mixtures thereof. Some of these classes are available both as thermosets and as thermoplastic polymers.

In some embodiments the stent or other portion of the assembly may include one or more areas, bands, coatings, members, etc. that is (are) detectable by imaging modalities such as X-Ray, MRI or ultrasound. In some embodiments at least a portion of the stent, sheath and/or adjacent assembly is at least partially radiopaque.

Catheter systems for delivery of multiple stents or stent segments are described in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; U.S. patent application Ser. No. 10/757,646, filed Jan. 13, 2004 and entitled Bifurcated Stent Delivery System; and U.S. patent application Ser. No. 10/784,337, filed Feb. 23, 2004 and entitled Apparatus and Method for Crimping a Stent Assembly; the entire content of each being incorporated herein by reference.

As used herein the term 'stent' refers to an expandable prosthesis for implantation into a body lumen or vessel and includes devices such as stents, grafts, stent-grafts, vena cava filters, etc. In some embodiments a stent may be at least partially constructed of any of a variety of materials such as stainless steel, nickel, titanium, nitinol, platinum, gold, chrome, cobalt, as well as any other metals and their combinations or alloys. A stent may be at least partially constructed of a polymer material. A stent may be at least partially constructed of a shape-memory polymer or material. A stent may be balloon expandable, self-expandable, hybrid expandable or a combination thereof. In some embodiments a stent or some other portion of the catheter may include one or more areas, bands, coatings, members etc that is (are) detectable by imaging modalities such as X-Ray, MRI or ultrasound. In some embodiments at least a portion of the stent is at least partially radiopaque. In some embodiments a stent may include one or more therapeutic and/or lubricious coatings applied thereto.

Embodiments of the present invention can be incorporated into those shown and described in the various references cited above. Likewise, embodiments of the inventions shown and described therein can be incorporated herein.

In the various embodiments described herein, the catheter assembly 10 may be a fixed wire catheter or any other catheter design.

The above materials throughout the application are intended for illustrative purposes only, and not as a limitation on the scope of the present invention. Suitable polymeric materials available for use are vast and are too numerous to be listed herein and are known to those of ordinary skill in the art.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A stent delivery system comprising:
a catheter including a proximal portion and a distal portion, the distal portion comprising a stent, the stent being expandable from a contracted configuration to an expanded configuration, the distal portion of the catheter further including a first tubular shaft and a second tubular shaft disposed within the stent, the first tubular shaft being spaced apart from and extending parallel to the second tubular shaft, and a balloon disposed around at least a portion of the first tubular shaft, the balloon having a contracted configuration and an expanded configuration, wherein, when the balloon is in the contracted configuration, the balloon includes a central body disposed about the first tubular shaft and only two wings, a first wing having a first portion and a second portion and a second wing having a first portion and a second portion, wherein the first portion of each of the first and second wings extends away from the central body and away from the first tubular shaft toward and on either side of the second tubular shaft, the first and second wings each having a fold such that the second portion of each of the first and second wings is folded upon the first portion, the second portions being folded such that the second portion of each wing extends inward on either side of the second tubular shaft and back toward the first tubular shaft, such that the second portion of each of the first and second wings is positioned adjacent the second tubular shaft, between the second tubular shaft and the first portion of the first and second wings, respectively, such that the second tubular shaft extends between the first and second wings, and a majority of balloon material is positioned on radially opposite sides of the first and second tubular shafts, resulting in the distal portion of the catheter, including the first and second tubular shafts and the folded balloon wings, having a substantially circular cross-section, wherein the first wing and the second wing extend radially from the central body.

2. The stent delivery system of claim 1, wherein the first and second wings curl inward toward the first tubular shaft.

3. The stent delivery system of claim 1, further comprising a first guide wire and a second guide wire, wherein the first guide wire is at least partially housed within the first tubular shaft and the second guide wire is at least partially housed within the second tubular shaft.

4. The stent delivery system of claim 1, wherein the stent comprises a proximal end and a distal end and an opening between the proximal and distal ends and wherein at least a portion of the second tubular shaft extends through the opening.

5. The stent delivery system of claim 1, wherein the stent is a bifurcated stent.

6. The stent delivery system of claim 1 wherein the balloon is symmetrical about a radial axis when in the contracted state.

7. A stent delivery system comprising:
a catheter, the catheter including a proximal portion and a distal portion, the distal portion comprising a stent, the stent being expandable from a contracted configuration to an expanded configuration, the distal portion of the catheter further including a first tubular shaft and a second shaft disposed with the stent, the first tubular shaft being spaced apart from and extending parallel to the second tubular shaft, and a balloon disposed about at least a portion of the first tubular shaft, wherein the distal portion of the catheter has a central longitudinal axis, wherein a portion of the balloon is between the first tubular shaft and the second shaft, the balloon having a contracted configuration and an expanded configuration;
wherein, when the balloon is in its contracted configuration, the balloon includes a central body and only two wings, wherein both first and second wings have a compound fold including a first portion extending away from the balloon central body and towards the second shaft, and a second portion extending inward next to a side of the second shaft towards the balloon central body, such that the first portion of each wing is folded upon the second portion of each wing, such that the second portion of each of the first and second wings extends on either side of the second tubular shaft such that the second portion of each of the first and second wings is positioned adjacent the second tubular shaft, between the second tubular shaft and the first portion of the first and second wings, respectively, such that the second tubular shaft extends between the first and second wings, the first wing and the second wing extending radially away from the central body;
wherein the catheter includes a first transverse axis extending radially through the longitudinal axis, and a second transverse axis extending perpendicular to the first transverse axis; and
wherein a majority of balloon material is positioned on axially extending opposite sides of the first and second tubular shafts, such that a width of the distal portion of the catheter including the first tubular shaft, the second shaft, and the folded balloon, measured along the first transverse axis, is substantially the same as a width of the distal portion of the catheter measured along the second transverse axis, such that the distal portion of the catheter has a substantially circular cross-section.

8. The stent delivery system of claim 7, wherein the stent is in its contracted configuration and is disposed about at least a portion of the first tubular shaft, at least a portion of the second shaft, and at least a portion of the balloon.

9. The stent delivery system of claim 7, further comprising a first guide wire and a second guide wire, wherein the first guide wire is at least partially housed within the first tubular shaft and the second guide wire is at least partially housed within the second shaft.

10. A stent delivery system comprising:
a catheter including a proximal portion and a distal portion, the distal portion comprising a stent, the stent being expandable from a contracted configuration to an expanded configuration, the distal portion of the catheter further comprising a first shaft and a second shaft disposed within the stent, the first tubular shaft being spaced apart from and extending parallel to the second tubular shaft, and a balloon disposed about at least a portion of the first shaft, wherein the first shaft has a first longitudinal axis and the second shaft has a second longitudinal axis, wherein a portion of the balloon is between the first shaft and the second shaft, the balloon having a contracted configuration and an expanded configuration;
wherein, when the balloon is in its contracted configuration, the balloon includes a central body, a first wing having first and second portions, and a second wing having first and second portions, the first portion of the first wing and the first portion of the second wing extending radially away from the central body and the second portion of the first wing and the second portion of the second wing extending towards the longitudinal axis of the catheter body such that a first wing end of the second portion of the first wing and a second wing end of the second portion of the second wing are positioned on opposite sides of the second shaft, the first wing and the second wing being disposed on radially opposite sides of the central body such that the second portion of each of the first and second wings is positioned adjacent the second shaft, between the second shaft and the first portion of the first and second wings, respectively, such that the second tubular shaft extends between the first and second wings; and
wherein the catheter includes a first transverse axis extending through the first longitudinal axis and second longitudinal axis in the distal portion, and a second transverse axis extending perpendicular to the first transverse axis, wherein when in the contracted state, a diameter of the balloon along the first transverse axis is substantially similar to a diameter of the balloon along the second transverse axis.

11. The stent delivery system of claim 10, wherein the first portion of each of the first and second wings extends towards the second shaft and a second portion of each of the first and second wings extends inward adjacent a side of the second shaft.

* * * * *